(12) United States Patent
Min et al.

(10) Patent No.: US 9,943,638 B2
(45) Date of Patent: Apr. 17, 2018

(54) CENTRIFUGATION SYSTEM WITH RED BLOOD CELL BARRIER

(71) Applicant: Fenwal, Inc., Lake Zurich, IL (US)

(72) Inventors: Kyungyoon Min, Kildeer, IL (US); Richard I. Brown, Northbrook, IL (US); John T. Foley, Wheeling, IL (US); Brian C. Case, Lake Villa, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 15/337,418

(22) Filed: Oct. 28, 2016

(65) Prior Publication Data

US 2017/0043080 A1 Feb. 16, 2017

Related U.S. Application Data

(62) Division of application No. 14/008,651, filed as application No. PCT/US2012/030869 on Mar. 28, 2012, now Pat. No. 9,533,089.

(Continued)

(51) Int. Cl.
   *B04B 5/04* (2006.01)
   *A61M 1/36* (2006.01)
   *C12N 5/078* (2010.01)

(52) U.S. Cl.
   CPC ........ *A61M 1/3693* (2013.01); *A61M 1/3696* (2014.02); *B04B 5/0442* (2013.01);
   (Continued)

(58) Field of Classification Search
   CPC .... A61M 1/3693; A61M 1/3696; A61M 1/38; B04B 5/0442; B04B 2005/045
   See application file for complete search history.

(56) References Cited

U.S. PATENT DOCUMENTS

| | | |
|---|---|---|
| 4,834,890 A | 5/1989 | Brown et al. |
| 5,076,911 A | 12/1991 | Brown et al. |

(Continued)

FOREIGN PATENT DOCUMENTS

| | | |
|---|---|---|
| WO | WO 01/66172 A2 | 9/2001 |
| WO | WO 2005/065834 A1 | 7/2005 |
| WO | WO 2012/141697 A1 | 10/2012 |

OTHER PUBLICATIONS

International Search Report and Written Opinion for PCT Patent Appl'n. No. PCT/US2012/030869, dated Jun. 28, 2012.

*Primary Examiner* — Timothy C Cleveland
(74) *Attorney, Agent, or Firm* — Cook Alex Ltd.

(57) ABSTRACT

Centrifugation systems and methods are provided for separating blood into its constituent parts. Inner and outer walls of a centrifuge each include a projection which extends toward the other wall. A separation chamber is received in the centrifuge between the walls, with the chamber including an inlet port for flowing blood into the chamber, a plasma outlet port for flowing plasma out of the chamber, and a red cell outlet port for flowing red blood cells out of the chamber. With the chamber received in the centrifuge between the walls, the first projection extends into the path of separated blood components flowing toward the plasma outlet port and prevents cellular blood components from flowing into the plasma outlet port. The second projection extends into the path of separated blood components flowing toward the red cell outlet port and prevents plasma from flowing into the red cell outlet port.

21 Claims, 11 Drawing Sheets

Related U.S. Application Data

(60) Provisional application No. 61/474,951, filed on Apr. 13, 2011.

(52) U.S. Cl.
CPC ......... *C12N 5/0634* (2013.01); *C12N 5/0641* (2013.01); *C12N 5/0644* (2013.01); *A61M 2205/128* (2013.01); *A61M 2205/3331* (2013.01); *A61M 2205/3337* (2013.01); *B04B 2005/045* (2013.01)

(56) References Cited

U.S. PATENT DOCUMENTS

| | | |
|---|---|---|
| 5,316,667 A | 5/1994 | Brown et al. |
| 5,573,678 A | 11/1996 | Brown et al. |
| 5,632,893 A | 5/1997 | Brown et al. |
| 5,693,232 A | 12/1997 | Brown et al. |
| 5,868,696 A | 2/1999 | Giesler et al. |
| 6,569,112 B2 | 5/2003 | Strahilevitz |

US 9,943,638 B2

CENTRIFUGATION SYSTEM WITH RED BLOOD CELL BARRIER

RELATED APPLICATION

This application is a divisional of U.S. patent application Ser. No. 14/008,651 filed Sep. 30, 2013, which is a U.S. national stage application of PCT Patent Application No. PCT/US12/30869 filed Mar. 28, 2012, which claims the benefit of U.S. provisional patent application Ser. No. 61/474,951 filed Apr. 13, 2011, all of which are hereby incorporated herein by reference.

TECHNICAL FIELD

The disclosure relates to blood treatment systems and methods. More particularly, the disclosure relates to systems and methods for separating blood into its constituents by centrifugation.

BACKGROUND

Various blood processing systems now make it possible to collect particular blood constituents, rather than whole blood, from donors or patients. Typically, in such systems, whole blood is drawn from a donor, the particular blood component or constituent is removed and collected, and the remaining blood constituents are returned to the donor. By thus removing only particular constituents, potentially less time is needed for the donor's body to return to pre-donation levels, and donations can be made at more frequent intervals than when whole blood is collected. This increases the overall supply of blood constituents, such as plasma and platelets, made available for health care.

Whole blood is typically separated into its constituents through centrifugation. This requires that the whole blood be passed through a centrifuge after it is withdrawn from, and before it is returned to, the donor. To avoid contamination and possible infection of the donor, the blood is preferably contained within a sealed, sterile fluid flow system during the entire centrifugation process. Typical blood processing systems thus include a permanent, reusable centrifuge assembly containing the hardware (drive system, pumps, valve actuators, programmable controller, and the like) that spins and pumps the blood, and a disposable, sealed and sterile fluid circuit that is mounted in cooperation on the hardware. The centrifuge assembly engages and spins a separation chamber of the disposable fluid circuit during a blood separation step. The blood, however, makes actual contact only with the fluid circuit, which assembly is used only once and then discarded.

As the whole blood is spun by the centrifuge, the heavier (greater specific gravity) components, such as red blood cells, move radially outwardly away from the center of rotation toward the outer or "high-G" wall of the separation chamber of the fluid circuit. The lighter (lower specific gravity) components, such as plasma, migrate toward the inner or "low-G" wall of the separation chamber. Various ones of these components can be selectively removed from the whole blood by forming appropriately located channeling seals and outlet ports in the separation chamber of the fluid circuit. For example, one application of therapeutic plasma exchange involves separating plasma from cellular blood components, collecting the plasma, and returning the cellular blood components and a replacement fluid to the donor.

After the blood has been separated into its constituent parts, it may be desirable to further process one more of the separated components. For example, in an alternative version of a therapeutic plasma exchange procedure, rather than replacing a patient's plasma with a different fluid, the patient's own plasma may be treated and returned after separation. This may be most efficiently achieved by pairing the blood separation system with a secondary processing device, such as an adsorption device or column. The adsorption device will remove undesirable substances from the plasma by immuno-adsorption. The exact substances removed depend upon the needs of the patient. For example, the substances removed from the plasma by the adsorption device may include low-density lipoproteins and Lipoprotein(a) for patients suffering from severe hypercholesterolemia. In another example, pathogenic antibodies may be removed from the plasma, for patients suffering from autoimmune diseases and organ transplant rejection, or as a pre-treatment before transplantation. In yet another example, fibrinogen, fibrin, and/or C-reactive protein may be removed from the plasma, for treating microcirculation disorders and ischemic tissue damage. Exemplary adsorption devices include the TheraSorb® line of products from Miltenyi Biotec GmbH Corporation of Bergisch Gladbach, Germany. Other examples of adsorption devices suitable for removing undesirable substances from plasma are described in greater detail in U.S. Pat. No. 6,569,112 to Strahilevitz, which is incorporated herein by reference.

One disadvantage of known centrifugation systems, particularly when used in therapeutic plasma exchange procedures, is that separated plasma in the centrifuge may flow into a return line for cellular blood components, rather than flowing into the plasma collection line. Such plasma in the wrong line will fail to be treated prior to return to the patient, meaning that the efficiency of the system is not only diminished, but there is a corresponding effect on the health benefits experienced by the patient. Another disadvantage of known centrifugation systems is that cellular blood components may flow into the plasma collection line, rather than flowing to the patient via a return line. Cellular blood components, such as platelets, in the separated plasma may have a negative effect on the health of the patient. Accordingly, the need remains for a centrifugation system with additional safety features and improved plasma collection efficiency with low cellular loss.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a centrifugation system is provided which includes the combination of a centrifuge and a separation chamber. The centrifuge is configured to separate blood components from blood by rotation about a rotational axis and comprises a generally annular low-G wall and a generally annular high-G wall which is located farther from the rotational axis than the low-G wall. The high-G wall includes a first projection extending toward the low-G wall and the low-G wall includes a second projection extending toward the high-G wall. The separation chamber includes multiple stages and is configured to be received in the centrifuge between the low-G and high-G walls. One of the stages of the separation chamber comprises an inlet port configured for flowing blood into the separation chamber, a plasma outlet port to transport a separated blood component substantially comprising plasma out of the separation chamber, and a red cell outlet port to transport a separated blood component substantially comprising red blood cells out of the separation chamber. When the separation chamber is received in the centrifuge between the low-G and high-G walls, the first projection is oriented so as to extend into the path of separated blood components flowing toward the plasma outlet port and prevent the separated blood component substantially comprising red blood cells from flowing into the plasma outlet port. The second projection is oriented so as to extend into the path of separated blood components flowing toward the red cell outlet port and prevent the separated blood component substantially comprising plasma from flowing into the red cell outlet port.

In another aspect, a centrifuge is provided for separating blood components from blood by rotation about a rotational axis. The centrifuge comprises a generally annular low-G wall and a generally annular high-G wall located farther from the rotational axis than the low-G wall. The high-G wall includes a first projection extending toward the low-G wall and the low-G wall includes a second projection extending toward the high-G wall. One end of the first projection is substantially angularly aligned with one end of the second projection.

In one aspect, a method is provided for centrifugally separating blood components from blood. The method includes flowing blood into a first stage of a multiple-stage separation chamber, the first stage having a plasma outlet port and a red cell outlet port. The separation chamber is rotated about a rotational axis so as to separate the blood into a separated blood component substantially comprising plasma and a blood component substantially comprising red blood cells. The separated blood components flow along a path toward the plasma outlet port, with the path including a first projection which is oriented to impede the separated blood component substantially comprising red blood cells from flowing into the plasma outlet port. The separated blood components also flow along a path toward the red cell outlet port, with the path including a second projection which is oriented to impede the separated blood component substantially comprising plasma from flowing into the red cell outlet port. One end of the first projection is substantially aligned with one end of the second projection along a radius passing through the rotational axis.

In another aspect, a method is provided for centrifugally separating blood components from blood. The method includes flowing blood into a first stage of a multiple-stage separation chamber, the first stage having a plasma outlet port and a red cell outlet port. The separation chamber is rotated about a rotational axis so as to separate the blood into a separated blood component substantially comprising plasma and a blood component substantially comprising red blood cells. The separated blood components flow along a path toward the plasma outlet port, with the path including a first projection which is oriented to impede the separated blood component substantially comprising red blood cells from flowing into the plasma outlet port. The separated blood components also flow along a path toward the red cell outlet port, with the path including a second projection which is oriented to impede the separated blood component substantially comprising plasma from flowing into the red cell outlet port. One end of the first projection is positioned directly adjacent to one end of the second projection.

In yet another aspect, a method is provided for centrifugally separating blood components from blood in a centrifuge including a generally annular low-G wall and a generally annular high-G wall located farther from a rotational axis of the centrifuge to define a channel therebetween. The method includes flowing blood into a first stage of a multiple-stage separation chamber at least partially received in the channel. The separation chamber is rotated about a rotational axis so as to separate the blood into a separated blood component substantially comprising plasma and a blood component substantially comprising red blood cells. The separated blood components flow along a path toward a plasma outlet port of the first stage, with the path including a first projection which is oriented to impede the separated blood component substantially comprising red blood cells from flowing into the plasma outlet port. The separated blood components also flow along a path toward a red cell outlet port of the first stage, with the path including a second projection which is oriented to impede the separated blood component substantially comprising plasma from flowing into the red cell outlet port. One end of the first projection is positioned substantially directly across the channel from one end of the second projection.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
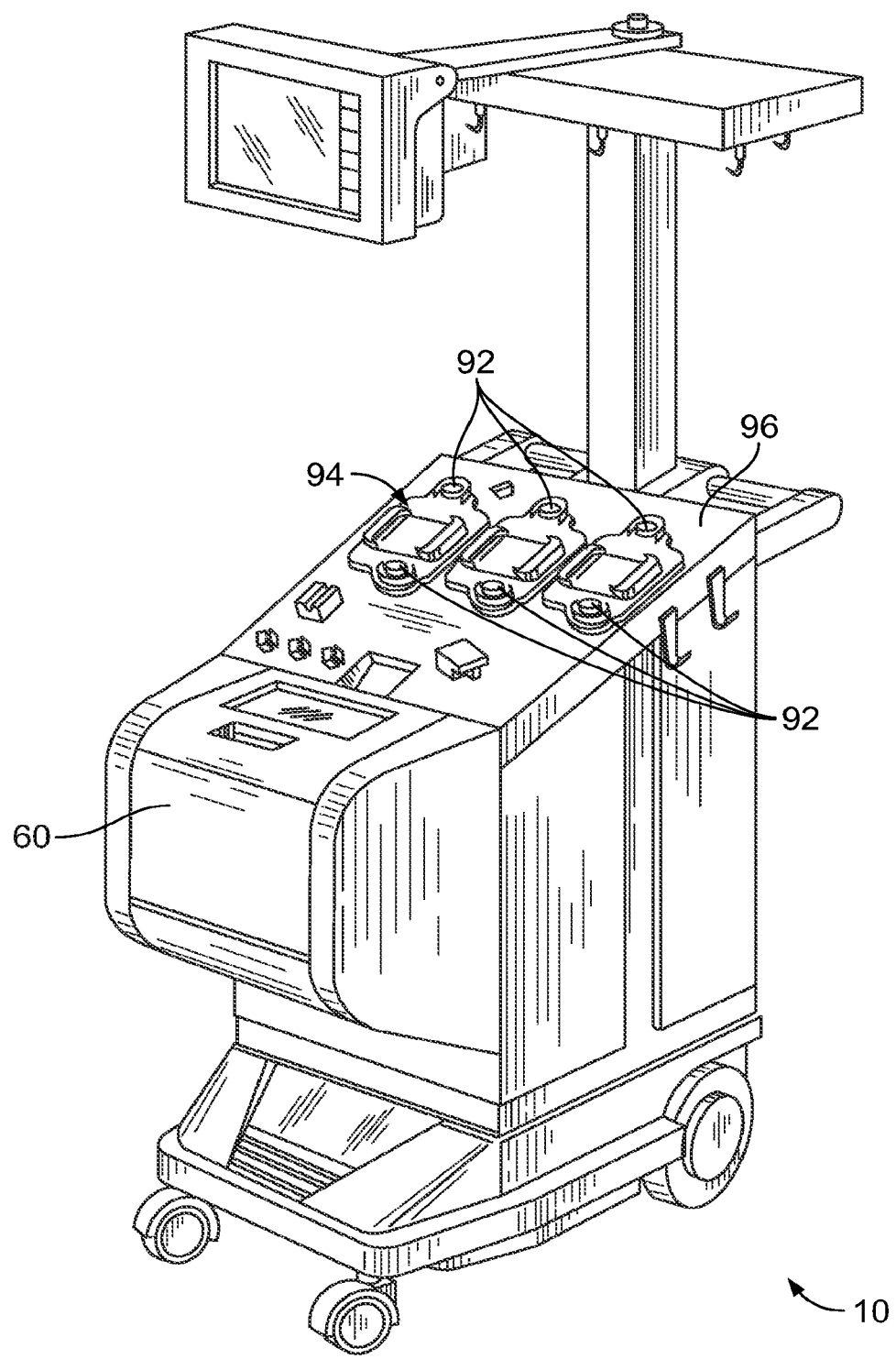
FIG. 1 is a perspective view of an exemplary fluid processing system of a blood separation system that may be used in combination with an adsorption device, in accordance with an aspect of the present disclosure.

FIG. 1 shows an exemplary fluid processing system 10 which is suitable for use with a centrifuge according to aspects of the present disclosure. The fluid processing system 10 may be provided generally according to known design, such as the system currently marketed as the AMICUS® separator by Fenwal, Inc. of Lake Zurich, Ill., which is an affiliate of Fresenius Kabi AG of Bad Homburg, Germany, as described in greater detail in U.S. Pat. No. 5,868,696, which is hereby incorporated herein by reference. The system 10 can be used for processing various fluids, but is particularly well suited for processing whole blood, blood components, or other suspensions of biological cellular materials. While improved centrifuges will be described herein with reference to one particular system 12, it should be understood that these principles may be employed with other fluid processing systems without departing from the scope of the present disclosure.

Figure 2:
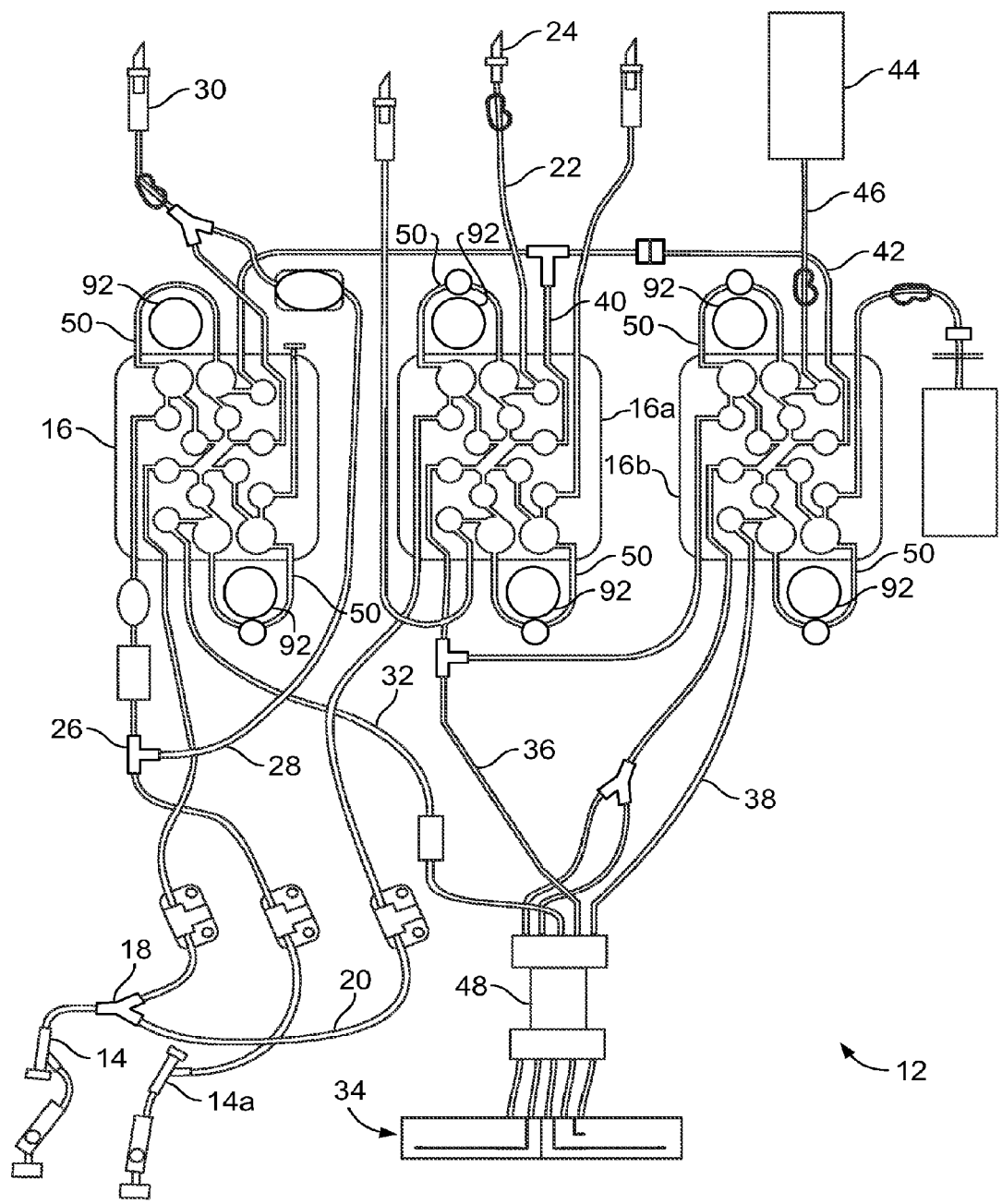
FIG. 2 is a diagrammatic view of an exemplary disposable flow circuit that may be used in combination with the fluid processing system of FIG. 1.

The fluid processing system 10 is used in combination with a single-use flow circuit 12, such as the one illustrated in FIG. 2, to form a centrifugation system. The flow circuit 12 includes a variety of tubing and a number of components, only some of which will be described herein in greater detail. The flow circuit 12 of FIG. 2 is specially configured to be used in combination with the fluid processing system 10 of FIG. 1, but it should be understood that the flow circuit may be differently configured if the fluid processing system is differently configured from the embodiment of FIG. 1.

Centrifuges according to the present disclosure are particularly useful in carrying out therapeutic plasma exchange procedures, but may be used in other fluid processing procedures as well. If employed for a therapeutic plasma exchange procedure, the fluid processing system 10 and flow circuit 12 will be used in combination with an adsorption device (not illustrated) which removes undesirable substances from separated plasma. Exemplary systems which pair a fluid processing system with an adsorption device are described in greater detail in PCT patent application no. PCT/US11/32320, filed Apr. 13, 2011, which is incorporated herein by reference.

A. The Flow Circuit

The illustrated flow circuit 12 is a "two needle" system, which includes a pair of blood source access devices 14 and 14a (e.g., phlebotomy needles) for fluidly connecting a blood source with the flow circuit 12. The blood source access devices 14 and 14a are connected by tubing to a left cassette 16, which will be described in greater detail herein. One of the blood source access devices 14 is used to draw blood from the blood source into the flow circuit 12 and is connected to the left cassette 16 by a y-connector 18. The other leg of the y-connector 18 is connected to tubing 20 which leads to a middle cassette 16a. The tubing 20 is connected, through the middle cassette 16a, to additional tubing 22, which includes a container access device 24 (e.g., a sharpened cannula or spike connector) for accessing the interior of an anticoagulant container (not illustrated). During a blood treatment operation, anticoagulant from the anticoagulant container is added to the blood from the blood source at the y-connector 18 prior to entering the left cassette 16.

The other blood source access device 14a is used to deliver or return blood, a blood component, and/or some other replacement fluid to the blood source and is also connected to the left cassette 16 by a y-connector 26. The other leg of the y-connector 26 is connected to tubing 28 connected at its other end to a container access device 30. Although not illustrated, the container access device 30 may be associated with a container having an amount of fluid (e.g., saline) to be used to prime the flow circuit 12 and/or delivered to the blood source via the blood source access device 14a.

The left cassette 16 also includes tubing 32 which is connected to a blood separation chamber 34 of the flow circuit 12 for flowing anticoagulated blood thereto. The blood separation chamber 34 separates the blood into its constituent parts (as will be described in greater detail herein) and returns the blood components to the flow circuit 12. In one embodiment, cellular blood components are returned to the middle cassette 16a of the flow circuit 12 from the blood separation chamber 34 via tubing 36, while substantially cell-free plasma is returned to a right cassette 16b of the flow circuit 12 from the blood separation chamber 34 via tubing 38. The cellular blood components may be pumped to the left cassette 16 via tubing 40, where they are returned to the blood source. The plasma may be pumped back to the left cassette 16 via tubing 42 for return to the blood source and/or it may be pumped into a container 44 via different tubing 46. The destination of the plasma (and the other fluids passing through the cassettes) depends upon the actuation of the various valves of the cassettes, as will be described in greater detail herein. The various tubing connected to the blood separation chamber 34 are bundled in an umbilicus 48, which will be described in greater detail herein.

Additional tubing may be connected from one port of a cassette to another port of the same cassette, so as to form tubing loops 50 which interact with a fluid flow element or pump to flow fluid through the flow circuit 12, as will be described in greater detail herein.

B. The Fluid Processing System

The fluid processing system 10 includes a centrifuge 52 (FIGS. 3 and 4) used to centrifugally separate blood components. The fluid processing system 10 may be programmed to separate blood into a variety of components (e.g., platelet-rich plasma and red cells). For illustrative purposes, a therapeutic plasma exchange procedure, in which the centrifuge 52 separates whole blood into cellular components (e.g., red blood cells and platelets) and substantially cell-free plasma, will be described herein. However, the principles described and claimed herein may be employed with other blood separation procedures without departing from the scope of the present disclosure.

Figure 3:
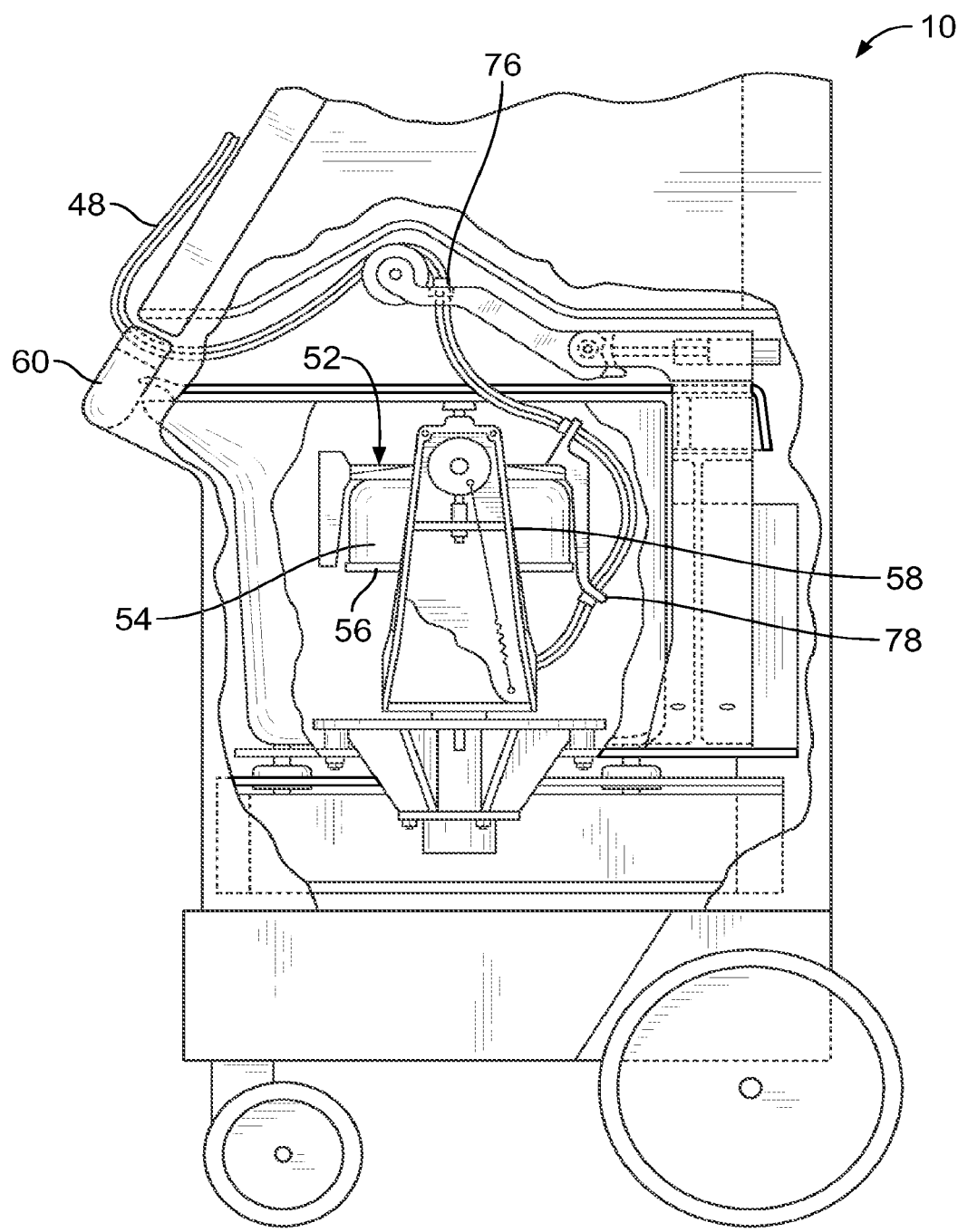
FIG. 3 is a side elevational view, with portions broken away and in section, of the fluid processing system of FIG. 1, with a centrifuge bowl and spool of the system being shown in their operating position.
Figure 4:
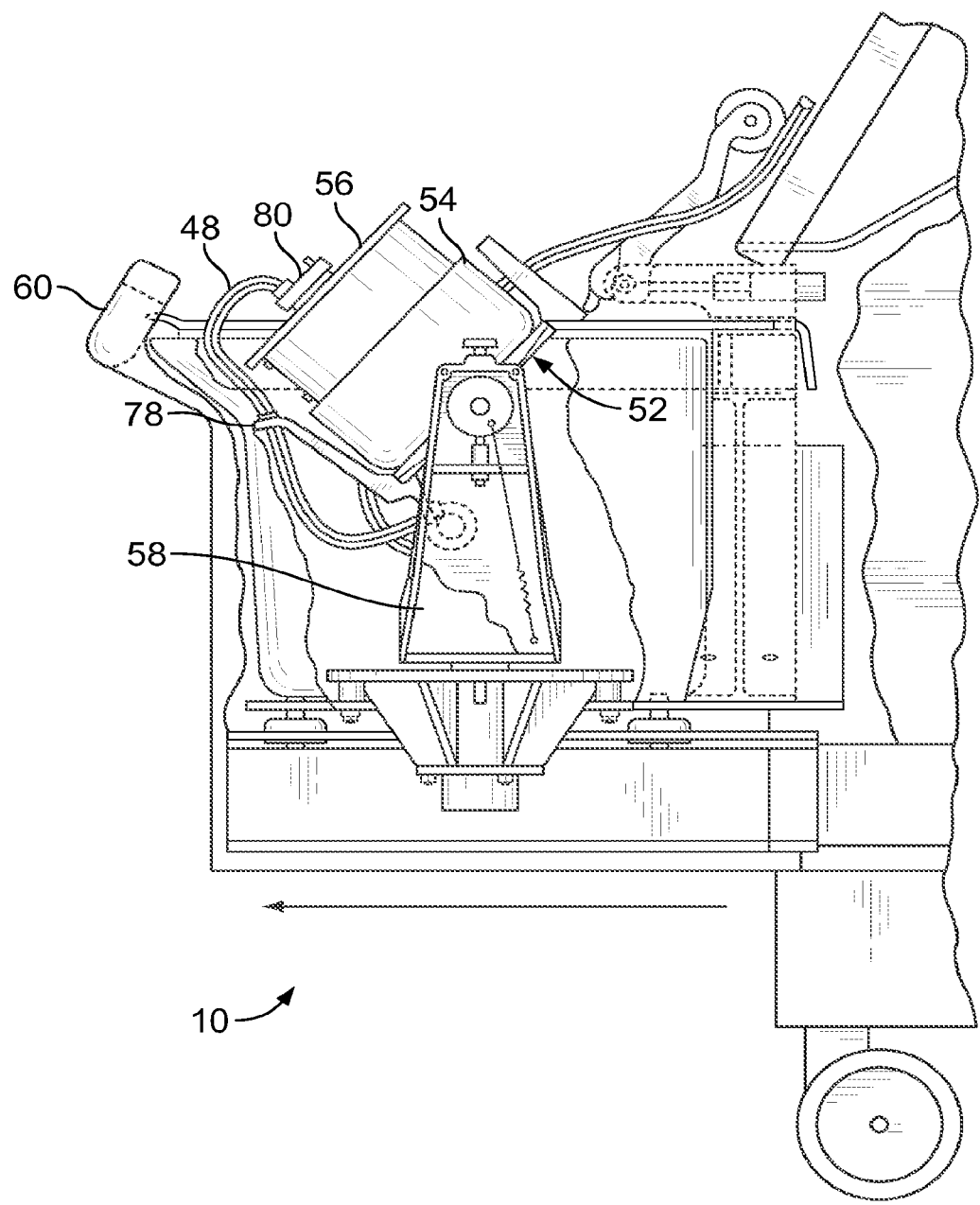
FIG. 4 is a side elevational view, with portions broken away and in section, of the fluid processing system of FIG. 1, with the centrifuge bowl and spool shown in an upright position for receiving a blood separation chamber.

The illustrated centrifuge 52 is generally of the type shown in U.S. Pat. No. 5,316,667 to Brown et al., which is incorporated herein by reference. The centrifuge 52 comprises a bowl 54 and a spool 56. The bowl 54 and spool 56 are pivoted on a yoke 58 between an operating position (FIG. 3) and a loading/unloading position (FIG. 4). The centrifuge 52 is housed within the interior of the fluid processing system 10, so a door 60 is provided to allow access to the centrifuge 52 for loading and unloading the blood separation chamber 34, as will be described in greater detail herein. The door 60 remains closed during operation to protect and enclose the centrifuge 52.

When in the loading/unloading position, the spool 56 can be opened by movement at least partially out of the bowl 54, as FIG. 4 shows. In this position, the operator wraps the flexible blood separation chamber 34 about the spool 56 (see FIG. 5). Closure of the spool 56 and bowl 54 encloses the chamber 34 for processing. When closed, the spool 56 and bowl 54 are pivoted into the operating position of FIG. 3 for rotation about a central rotational axis.

C. The Blood Separation Chamber

Figure 6:
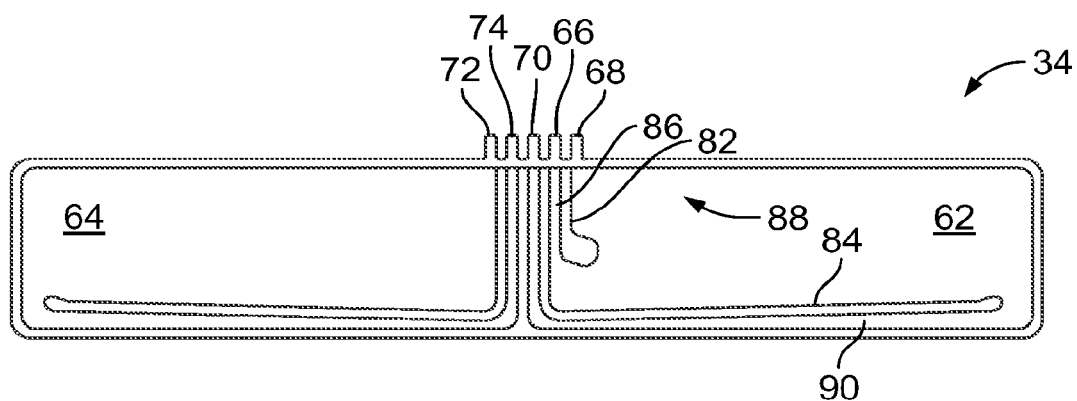
FIG. 6 is a plan view of the blood separation chamber of FIG. 5, out of association with the spool.

FIG. 6 shows a representative embodiment of a multiple-stage blood separation chamber 34 which may be used in connection with centrifuges according to the present disclosure. The chamber 34 shown in FIG. 6 allows for either single- or multi-stage processing. When used for multi-stage processing, a first stage 62 separates whole blood into first and second components. Depending on the nature of the separation procedure, one of the components may be transferred into a second stage 64 for further processing.

Figure 5:
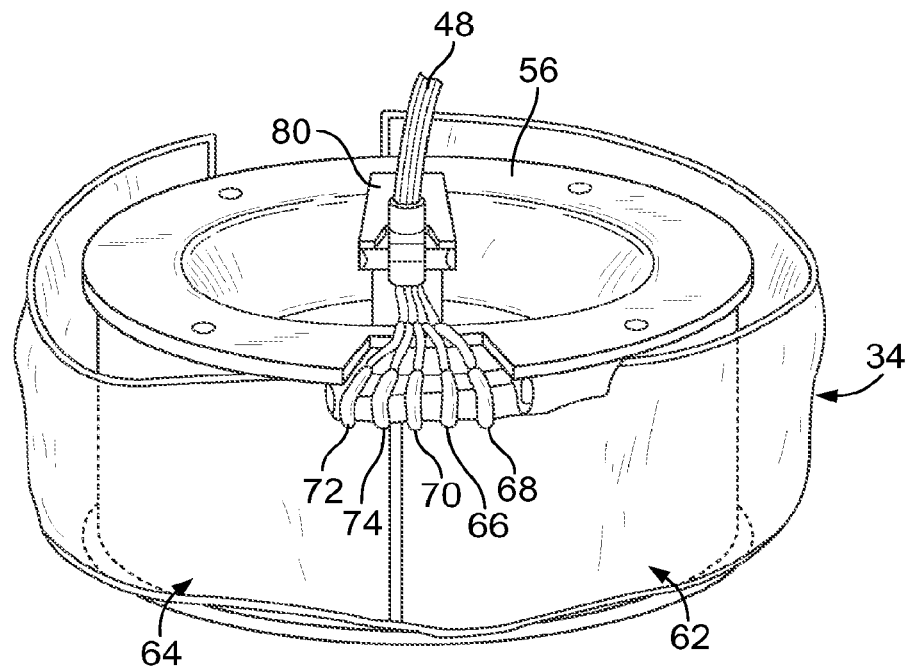
FIG. 5 is a top perspective view of the spool of the fluid processing system of FIG. 4 in its upright position and carrying the blood separation chamber of the flow circuit of FIG. 2.

As FIGS. 5 and 6 best show, there are three ports 66, 68, and 70 associated with the first stage 62. Depending on the particular blood processing procedure, the ports may have different functionality but, in a therapeutic plasma exchange procedure, the port identified at 70 is used for conveying blood from a blood source into the first stage 62 (via tubing 32 of the flow circuit 12). During such a therapeutic plasma exchange procedure, the other two ports 66 and 68 serve as outlet ports for passing separated blood components from the first stage 62 to the flow circuit 12 (via tubing 36 and 38, respectively). More particularly, the first outlet port 68 conveys a low density blood component from the first stage 62, while the second outlet port 66 conveys a high density blood component from the first stage 62.

In a method of carrying out single-stage processing, one of the separated components is returned to the blood source, while the other is removed from the first stage 62 for further processing via an adsorption device, as will be described in greater detail herein. For example, when carrying out a therapeutic plasma exchange procedure, whole blood in the first stage 62 is separated into cellular components (i.e., a high density component) and substantially cell-free plasma (i.e., a low density component). The plasma is removed from the first stage 62 via the first outlet port 68 for further processing by the adsorption device, while the cellular components are removed from the first stage 62 via the second outlet port 66 and returned to the blood source. After the plasma has been treated by the adsorption device, it may be returned to the blood source.

If multi-stage processing is required, one of the components will be transferred from the first stage 62 to the second stage 64 via a port 72 associated with the second stage 64. The component transferred to the second stage 64 is further fractionated into sub-components, with one of the sub-components being removed from the second stage 64 via an outlet port 74 and the other sub-component remaining in the second stage 64. In the illustrated embodiment, the ports 66, 68, 70, 72, and 74 are arranged side-by-side along the top transverse edge of the chamber 34.

While the same ports 66, 68, and 70 of the first stage 62 are used as in the above-described therapeutic plasma exchange procedure, the ports 66 and 70 have different functionality in a multi-stage separation procedure. In one method of multi-stage operation, blood enters the first stage 62 via the port 66 and is separated into red blood cells (i.e., the high density blood component) and platelet-rich plasma (i.e., the low density blood component). The red blood cells are returned to the blood source (via the port 70), while the platelet-rich plasma is conveyed out of the first stage 62 (via the first outlet port 68) and into the second stage 64 (via the inlet port 72). In the second stage 64, the platelet-rich plasma is separated into platelet-poor plasma and platelet concentrate. The platelet-poor plasma is removed from the second stage 64 (via the outlet port 74), leaving platelet concentrate in the second stage 64 for resuspension and transfer to one or more storage containers.

As best shown in FIG. 5, the tubing umbilicus 48 of the flow circuit 12 is attached to the ports 66, 68, 70, 72, and 74. The umbilicus 48 interconnects the first and second stages 62 and 64 with each other and with the components of the flow circuit 12 positioned outside of the centrifuge 52. As FIG. 3 shows, a non-rotating (zero omega) holder 76 holds the upper portion of the umbilicus 48 in a non-rotating position above the spool 56 and bowl 54. A holder 78 on the yoke 58 rotates the mid-portion of the umbilicus 48 at a first (one omega) speed about the suspended spool 56 and bowl 54. Another holder 80 (FIGS. 4 and 5) rotates the lower end of the umbilicus 48 at a second speed twice the one omega speed (the two omega speed), at which two omega speed the umbilicus 48 drives the rotation of the spool 56 and bowl 54. This known relative rotation of the umbilicus 48 keeps it untwisted, in this way avoiding the need for rotating seals.

As FIG. 6 shows, a first interior seal 82 is located between the low density or plasma outlet port 68 and the high density or red cell outlet port 66. A second interior seal 84 is located between the high density outlet port 66 and the blood inlet port 70. The interior seals 82 and 84 form a fluid path or passage 86 (an outlet for high density blood components in a therapeutic plasma exchange procedure) and a low density collection path or region 88 in the first stage 62. The second seal 84 also forms a fluid passage 90 (a blood inlet in a therapeutic plasma exchange procedure) in the first stage 62.

D. The Cassettes

Blood entering the blood separation chamber 34 is pumped thereinto by one or more pumps 92 of the fluid processing system 10 (FIGS. 1 and 2) acting upon one or more of the tubing loops 50 extending from the cassettes 16-16*b* of the flow circuit 12 (FIG. 2). An exemplary cassette 16 is illustrated in greater detail in FIGS. 7 and 8, while the pumps 92 and associated cassette holder 94 are shown in greater detail in FIG. 9.

Before beginning a given blood processing and collection procedure, the operator loads various components of the flow circuit 12 onto the sloped front panel 96 and centrifuge 52 of the centrifuge system 10. As described above, the blood separation chamber 34 and the umbilicus 48 of the flow circuit 12 are loaded into the centrifuge 52, with a portion of the umbilicus 48 extending outside of the interior of the centrifuge system 10, as shown in FIG. 3. The sloped front panel 96 of the centrifuge system 10 includes at least one cassette holder 94 (three in the illustrated embodiment), each of which is configured to receive and grip an associated cassette 16-16*b* of the flow circuit 12.

Figure 7:
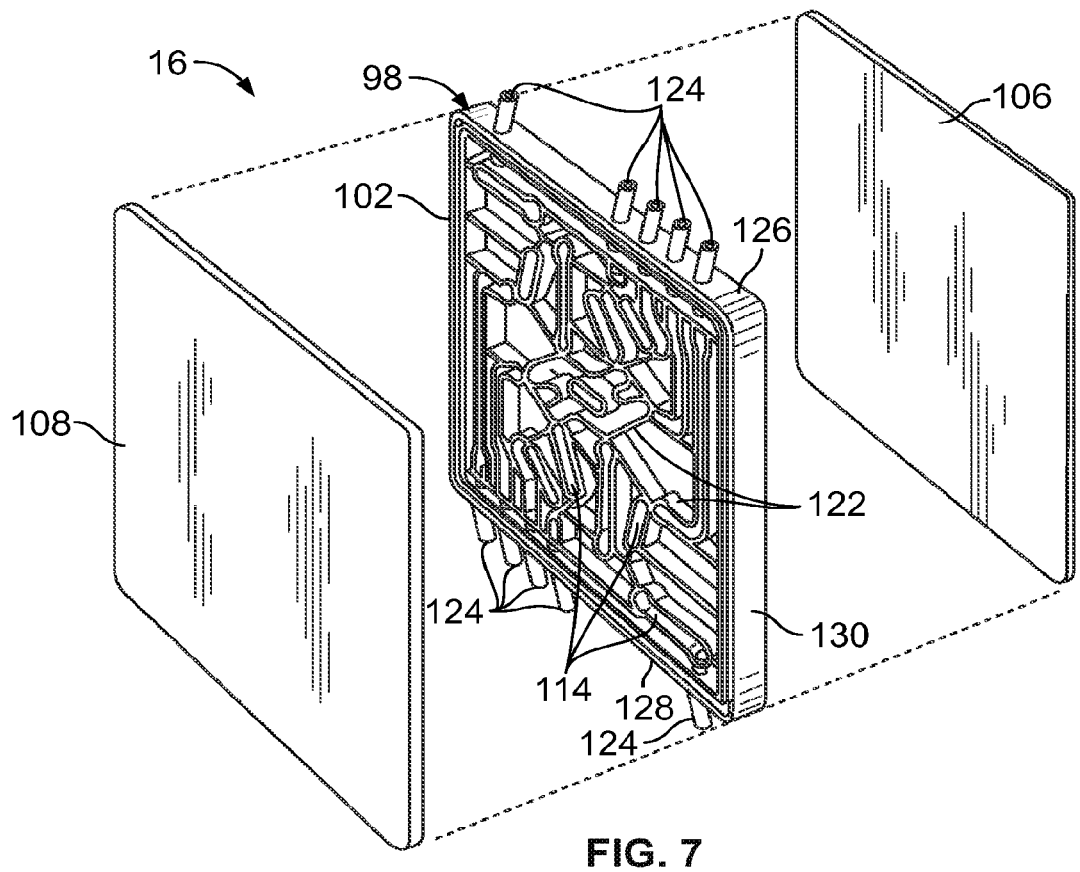
FIG. 7 is an exploded perspective view of a fluid processing cassette of the flow circuit of FIG. 2.
Figure 8:
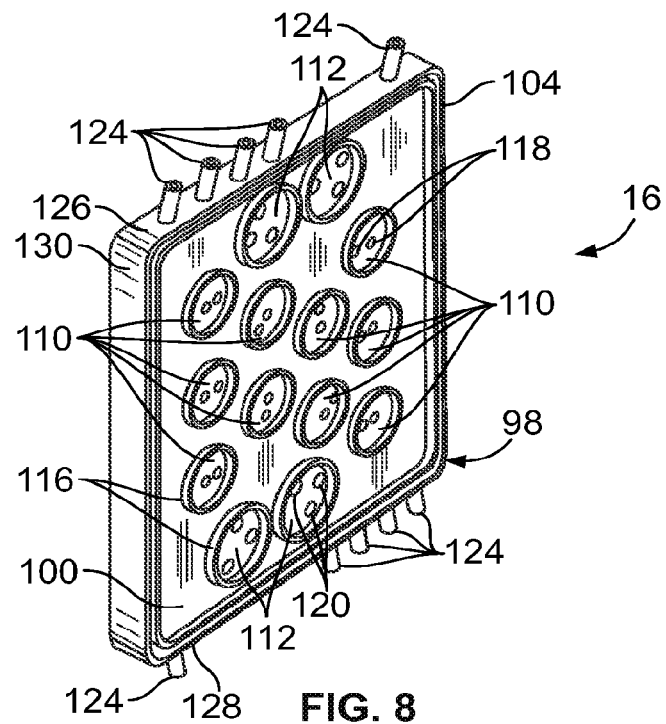
FIG. 8 is a perspective view of an underside of the fluid processing cassette of FIG. 7.
Figure 9:
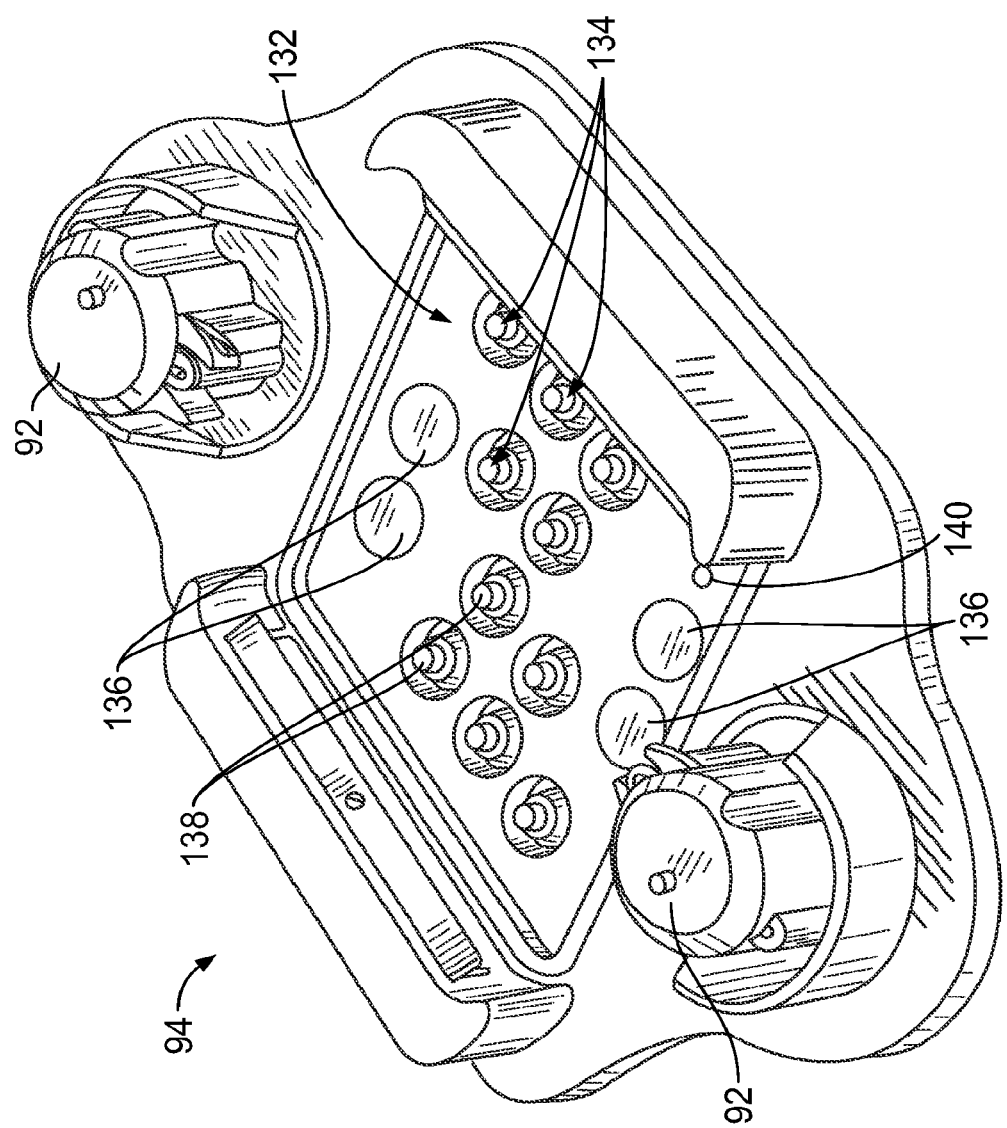
FIG. 9 is a perspective view of a cassette holder of the fluid processing system of FIG. 1.

Each cassette 16-16*b*, one of which is shown in FIGS. 7 and 8, includes an injection molded body 98 that is compartmentalized by an interior wall 100 (FIG. 8) to present or form a topside 102 (FIG. 7) and an underside 104 (FIG. 8). For the purposes of description, the topside 102 is the side of the cassette 16 that, in use, faces away from the centrifuge system 10, while the underside 104 faces towards the centrifuge system 10. A flexible diaphragm 106 overlies and peripherally seals the underside 104 of the cassette 16. A generally rigid upper panel 108 overlies the topside 102 of the cassette 16 and is sealed peripherally and to the raised channel-defining walls in the cassette 16, as described later.

In one embodiment, the cassette 16, the interior wall 100, and the upper panel 108 are made of a rigid medical grade plastic material, while the diaphragm 106 is made of a flexible sheet of medical grade plastic. The upper panel 108 and the diaphragm 106 are sealed about their peripheries to the peripheral edges of the top- and undersides 102, 104 of the cassette 16, respectively.

As shown in FIGS. 7 and 8, the top- and undersides 102, 104 of the cassette 16 contain preformed cavities. On the underside 104 of the cassette 16 (FIG. 8), the cavities form an array of valve stations 110 and an array of pressure sensing stations 112. On the topside 102 of the cassette 16 (FIG. 7), the cavities form an array of channels or paths 114 for conveying liquids. The valve stations 110 communicate with the liquid paths 114 through the interior wall 100 to interconnect them in a predetermined manner. The sensing stations 112 also communicate with the liquid paths 114 through the interior wall 100 to sense pressures in selected regions. The number and arrangement of the liquid paths 114, the valve stations 110, and the sensing stations 112 can vary but, in the illustrated embodiment, the cassette 16 provides nineteen liquid paths 114, ten valve stations 110, and four sensing stations 112.

The valve and sensing stations 110, 112 resemble shallow wells open on the cassette underside 104 (FIG. 8). Upstanding edges 116 rise from the interior wall 100 and peripherally surround the valve and sensing stations 110, 112. The valve stations 110 are closed by the interior wall 100 on the topside 102 of the cassette 16, except that each valve station 110 includes a pair of through holes or ports 118 in the interior wall 100. The ports 118 each open into selected different liquid paths 114 on the topside 102 of the cassette 16.

The sensing stations 112 are likewise closed by the interior wall 100 on the topside 102 of the cassette 16, except that each sensing station 112 includes three through holes or ports 120 in the interior wall 100 (FIG. 8). The ports 120 open into selected liquid paths 114 on the topside 102 of the cassette 16. These ports 120 channel liquid flow among the selected liquid paths 114 through the associated sensing station 112.

In one embodiment, the flexible diaphragm 106 overlying the underside 104 of the cassette 16 is sealed by ultrasonic welding to the upstanding peripheral edges 116 of the valve and sensing stations 110, 112. This isolates the valve stations 110 and sensing stations 112 from each other and the rest of the system. In an alternative embodiment, the flexible diaphragm 106 can be seated against the upstanding edges 116 by an external positive force applied by the cassette holder 94 against the diaphragm 106. The positive force, like the ultrasonic weld, peripherally seals the valve and sensing stations 110, 112.

The localized application of additional positive force (referred to herein as a "closing force") upon the intermediate region of the diaphragm 106 overlying a valve station 110 serves to flex the diaphragm 106 into the valve station 110. Such closing force is provided by the cassette holder 94, as will be described in greater detail herein. The diaphragm 106 seats against one of the ports 118 to seal the port 118, which closes the valve station 110 to liquid flow. Upon removal of the closing force, fluid pressure within the valve station 110, the application of a vacuum to the outer surface of the diaphragm 106, and/or the plastic memory of the diaphragm 106 itself unseats the diaphragm 106 from the port 118, opening the valve station 110 to liquid flow.

Upstanding channel sides or edges 122 rise from the interior wall 100 to peripherally surround and define the liquid paths 114, which are open on the topside 102 of the cassette 16. The liquid paths 114 are closed by the interior wall 100 on the underside 104 of the cassette 16, except for the ports 118, 120 of the valve and sensing stations 110, 112 (FIG. 8). The rigid panel 108 overlying the topside 102 of the cassette 16 is sealed by ultrasonic welding to the upstanding peripheral edges 122, sealing the liquid paths 114 from each other and the rest of the system.

In the illustrated embodiment, ten pre-molded tube connectors 124 extend out along opposite side edges 126, 128 of each cassette 16. The tube connectors 124 are arranged five on one side edge 126 and five on the other side edge 128. The other side edges 130 of the cassette 16, as illustrated, are free of tube connectors. The tube connectors 124 are associated with external tubing (FIG. 2) to associate the cassettes 16 with the remainder of the flow circuit 12, as described above.

The tube connectors 124 communicate with various interior liquid paths 114, which constitute the liquid paths of the cassette 16 through which a fluid enters or exits the cassette 16. The remaining interior liquid paths 114 of the cassette 16 constitute branch paths that link the liquid paths 114 associated with the tube connectors 124 to each other through the valve stations 110 and sensing stations 112.

E. The Cassette Holders And Pumps

Turning now to the cassette holders 94 (FIG. 9), each receives and grips one of the cassettes 16-16*b* along the two opposed sides edges 130 in the desired operating position. The cassette holder 94 includes a pair of peristaltic pump stations 92. When the cassette 16 is gripped by the cassette holder 94, tubing loops 50 extending from the cassette 16 (FIG. 2) make operative engagement with the pump stations 92. The pump stations 92 are operated to cause fluid flow through the cassette 16.

The flexible diaphragm 106 covering the underside 104 of the cassette 16 is urged into intimate contact with a valve and sensor array or assembly 132 by the cassette holder 94. The valve assembly 132 acts in concert with the valve stations 110 and sensing stations 112 of the cassette 16. The valve assembly 132 illustrated in FIG. 9 includes ten valve actuators 134 and four pressure sensing transducers 136. The valve actuators 134 and the pressure sensing transducers 136 are mutually arranged in the same layout as the valve stations 110 and sensing stations 112 on the underside 104 of the cassette 16. When the cassette 16 is gripped by the cassette holder 94, the valve actuators 134 align with the cassette valve stations 110. At the same time, the pressure sensing transducers 136 mutually align with the cassette sensing stations 112.

In one embodiment, each valve actuator 134 includes an electrically actuated solenoid pin or piston 138. Each piston 138 is independently movable between an extended position and a retracted position. When in its extended position, the piston 138 presses against the region of the diaphragm 106 that overlies the associated valve station 110. In this position, the piston 138 flexes the diaphragm 106 into the associated valve station 110, thereby sealing the associated valve port 118. This closes the valve station 110 to liquid flow. When in its retracted position, the piston 138 does not apply force against the diaphragm 106. As before described, the plastic memory of the diaphragm 106 may be such that the removal of force is sufficient for the diaphragm to unseat from the valve port 118, thereby opening the valve station 110 to liquid flow. Alternatively, a vacuum may be applied to the diaphragm 106, for example by the vacuum port 140 illustrated in FIG. 9, to actively unseat the diaphragm 106 from the valve port 118.

The pressure sensing transducers 136 sense liquid pressures in the sensing stations 112 of the cassette 16. The sensed pressures are transmitted to a controller of the centrifuge system 10 as part of its overall system monitoring function. If provided, the vacuum port 140 of the cassette holder 94 may provide suction to the diaphragm 106 of the cassette 16, drawing it into close contact with the transducers 136 for more accurate pressure readings.

F. Blood Separation

As described above, the centrifuge 52 rotates the blood separation chamber 34, thereby centrifugally separating whole blood received from a blood source into component parts, e.g., red blood cells, plasma, and buffy coat comprising platelets and leukocytes.

Figure 10:
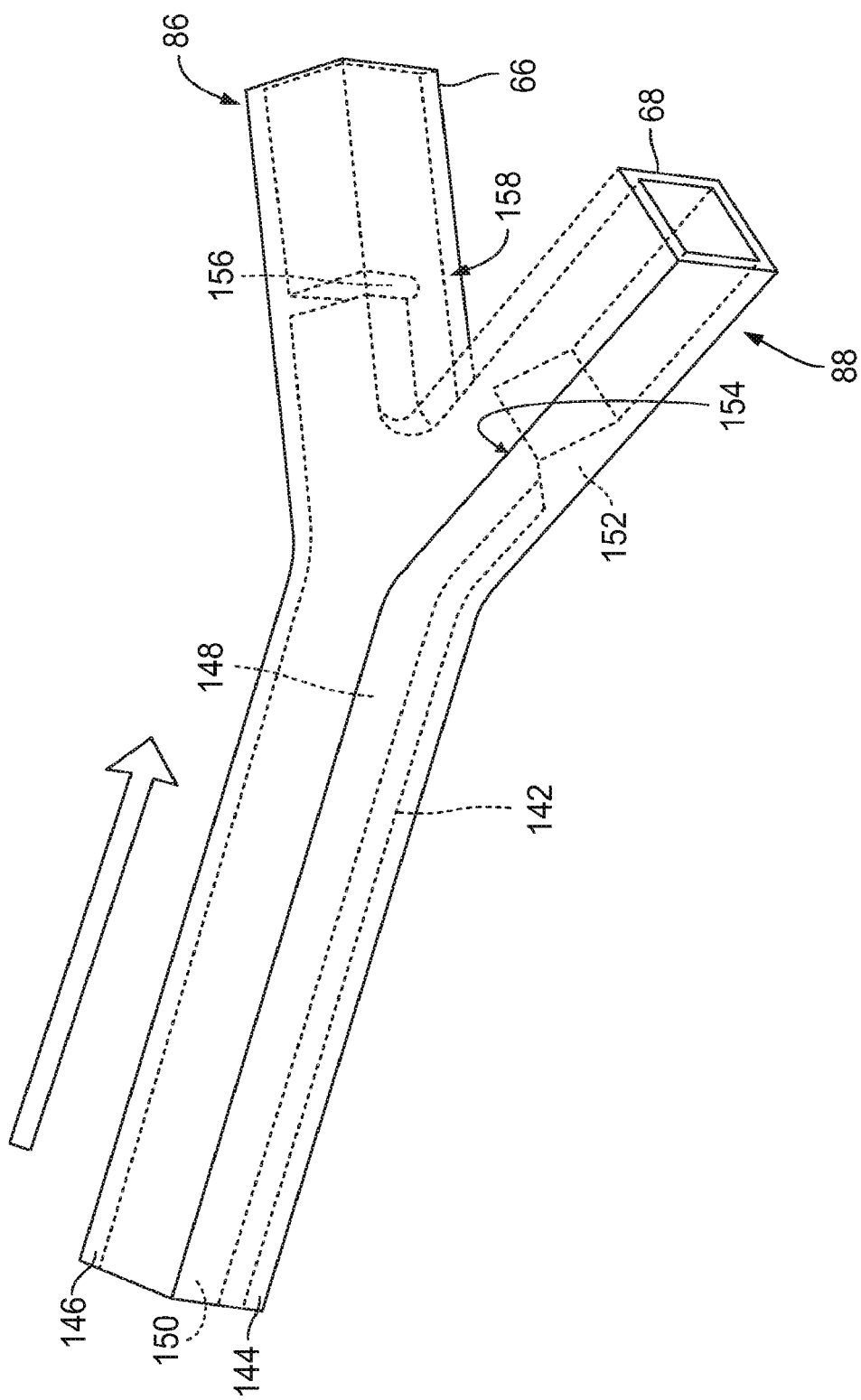
FIG. 10 is a diagrammatic view of blood flowing through a first stage of the blood separation chamber of FIG. 6, with the blood being centrifugally separated into a red blood cell layer, plasma layer, and interface within the chamber.

In a therapeutic plasma exchange procedure, the fluid passage 90 channels blood directly into the region upstream of the flow path 86 leading to the red cell outlet port 66 and the flow path 88 leading to the plasma outlet port 68. As shown in FIG. 10, the blood separates into an optically dense layer 142 containing cellular components, which forms as cellular components move under the influence of centrifugal force toward the high-G (outer) wall 144. The optically dense layer 142 will be substantially comprised of red blood cells (and, hence, will be referred to herein as the "RBC layer") but, depending on the speed at which the centrifuge 52 is spun, other cellular components (e.g., larger white blood cells and platelets) may also be present in the RBC layer 142.

The movement of the component(s) of the RBC layer 142 displaces less dense blood components radially toward the low-G (inner) wall 146, forming a second, less optically dense layer 148. The less optically dense layer 148 is substantially comprised of plasma (and, hence, will be referred to herein as the "plasma layer") but, depending on the speed at which the centrifuge 52 is rotated and the length of time that the blood is resident in the centrifuge, other components (e.g., platelets and smaller white blood cells) may also be present in the plasma layer 148.

The transition between the formed cellular blood components and the liquid plasma component is generally referred to as the interface 150 (FIG. 10). Platelets and white blood cells (which have a density greater than plasma and usually less than red blood cells) typically occupy this transition region, although that also varies with centrifuge speed and residence time, as is well known in the technical field.

Figure 11:
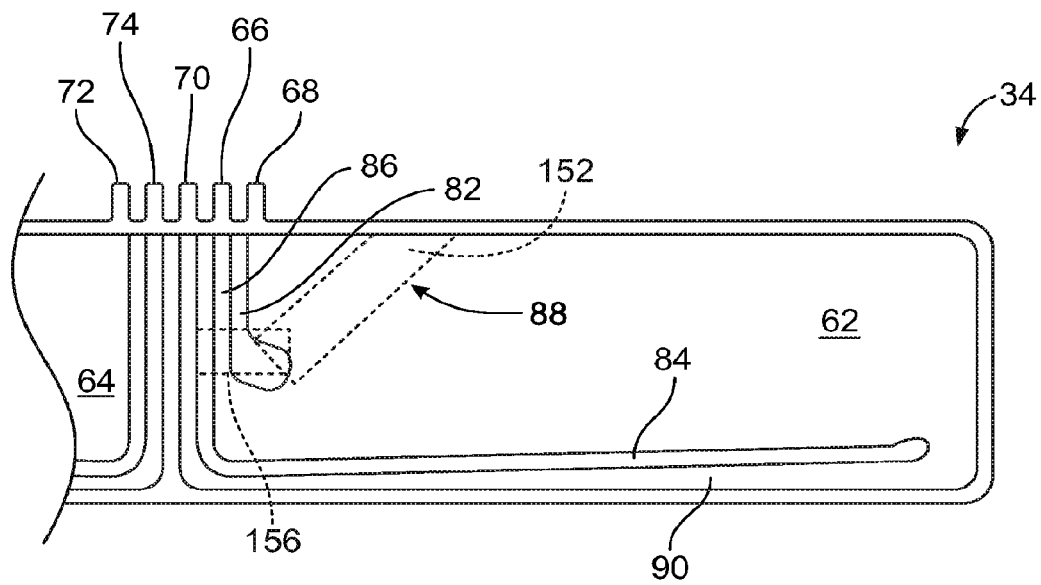
FIG. 11 is a plan view of the first stage of the blood separation chamber of FIG. 6, with first and second projections of the associated centrifuge shown in broken lines.
Figure 12:
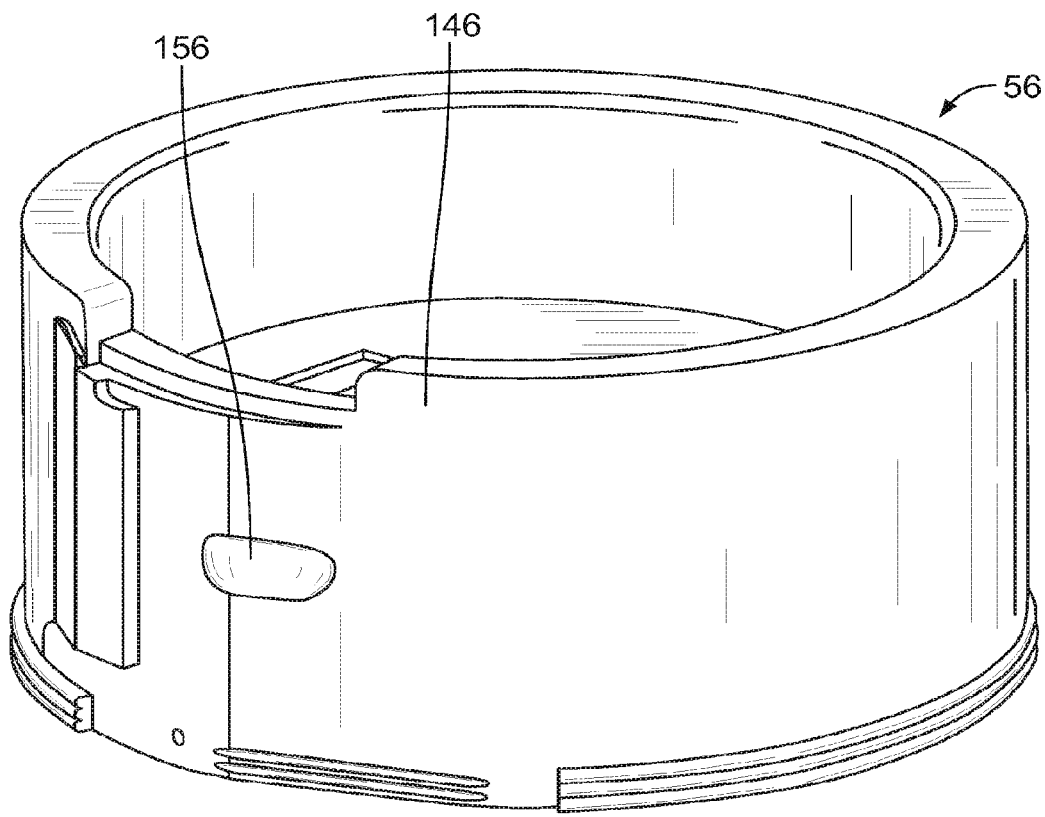
FIG. 12 is a perspective view of the centrifuge spool of the fluid processing system of FIG. 1.

As FIGS. 10 and 11 show, a first projection or ramp 152 extends from the high-G wall 144 of the bowl 54 at an angle across the path 88 to the plasma outlet port 68. The angle, measured with respect to the rotational axis of the centrifuge 52 or the axis of the first outlet port 68 is about 30° in one embodiment. FIG. 11 shows, in phantom lines, the orientation of the ramp 152 when viewed from the high-G wall 144 of the bowl 54. Further details of the angled relationship of the ramp 152 and the first outlet port 68 can be found in U.S. Pat. No. 5,632,893 to Brown et al., which is incorporated herein by reference.

The ramp 152 forms a tapered wedge that restricts the flow of fluid toward the first outlet port 68. The top edge of the ramp 152 extends to form a constricted passage 154 along the low-G wall 146. The plasma layer 148 must flow through the constricted passage 154 to reach the first outlet port 68. The location of the interface 150 on the ramp 152 (FIG. 10) can dynamically shift during blood processing. If the location of the interface 150 is too high (that is, if it is too close to the low-G wall 146), cellular components can spill over the ramp 152 and into the plasma outlet port 68, adversely affecting the quality of the low density components (typically plasma). On the other hand, if the location of the interface 150 on the ramp 152 is too low (that is, if it resides too far away from the low-G wall 146), the collection efficiency of the centrifuge system 10 may be impaired. The fluid processing system 10 may employ an interface control system which optically monitors the location of the interface 150 on the ramp and adjusts the operation of the fluid processing system 10 (e.g., changing the rate at which plasma is drawn out of the blood separation chamber 34) to adjust the interface 150 to the optimal location.

Figure 13:
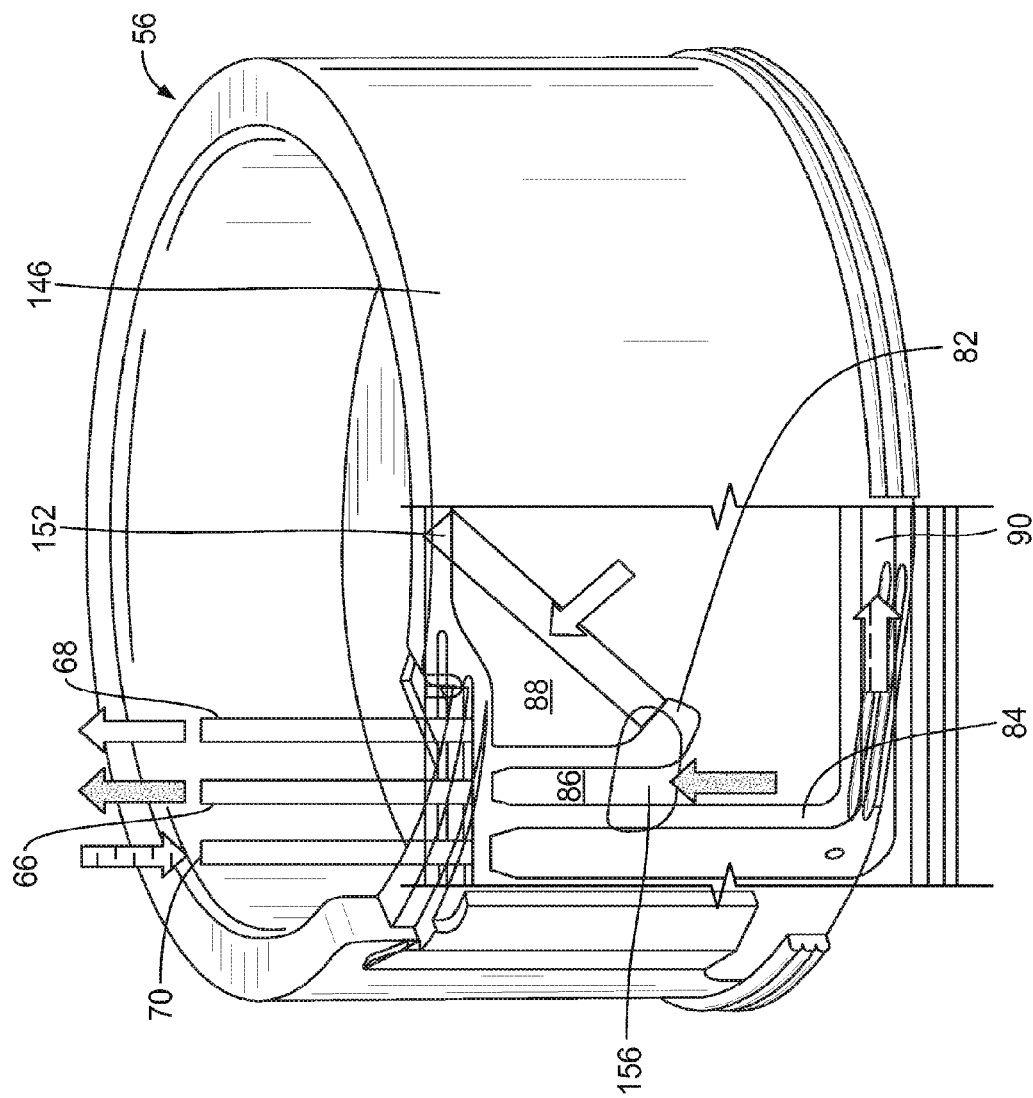
FIG. 13 is a perspective view of the centrifuge spool of the centrifuge system of FIG. 1, shown with a portion of the blood separation chamber of FIG. 6 overlaying the spool.

As FIGS. 10-14 show, a second projection or red blood cell barrier 156 which extends from the low-G wall 146 or the spool 56 across at least a portion of the path 86 to the red cell outlet port 66. More preferably, the second projection 156 extends across the entirety of the path 86 to the red cell outlet port 66, as shown in FIGS. 11 and 13, such that the separated blood components must cross one of the projections 152, 156 prior to exiting the first stage 62 of the blood separation chamber 34. In the illustrated embodiment, the second projection 156 is generally rectangular or elliptical, having a width greater than its axial height, and is oriented substantially horizontally (i.e., generally perpendicular to the rotational axis of the centrifuge 52 or the axis of the red cell outlet port 66), although other configurations and/or orientations may also be employed without departing from the scope of the present disclosure.

Figure 14:
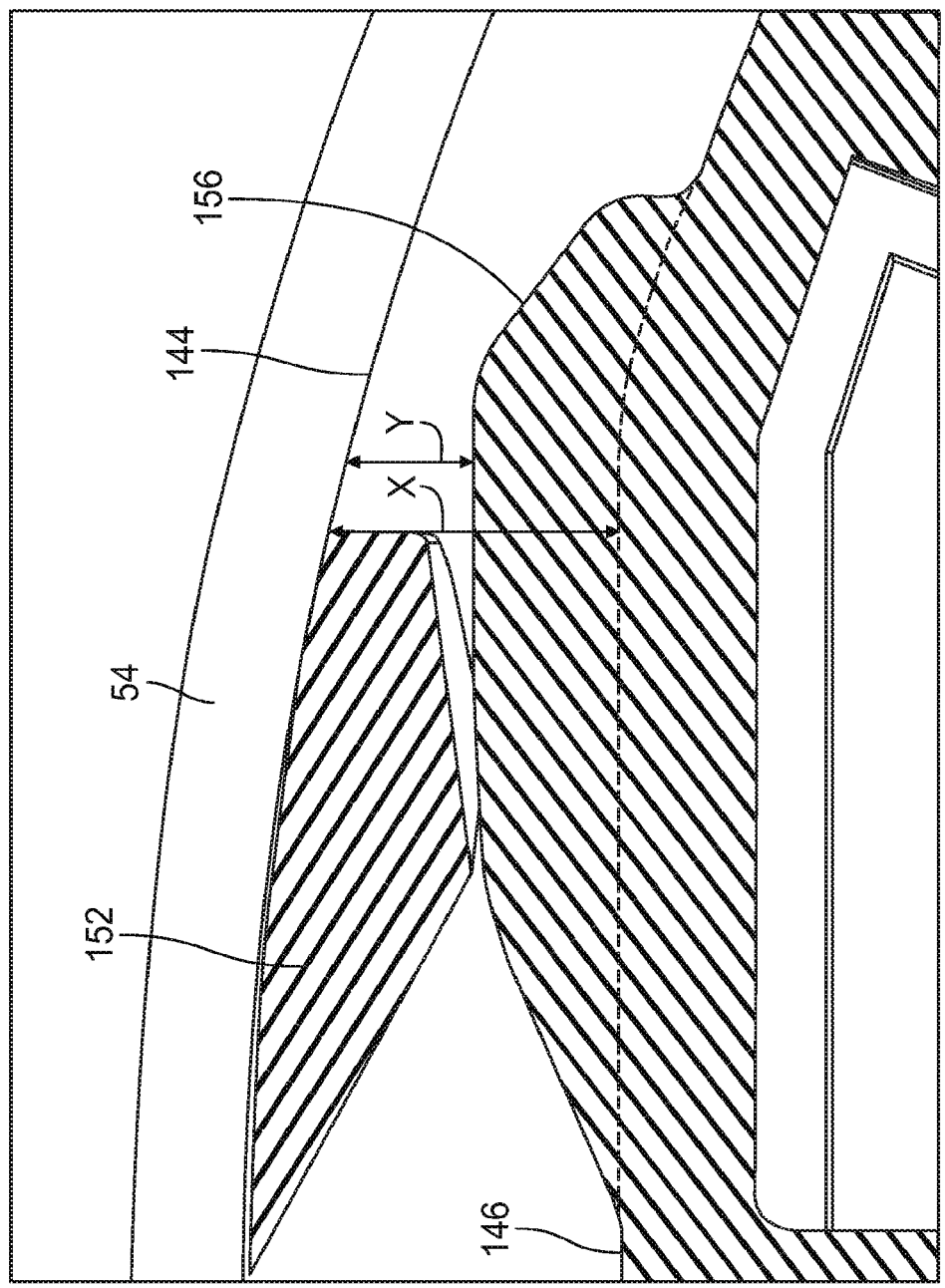
FIG. 14 is a cross-sectional top plan view of a portion of the centrifuge, showing the first and second projections.

The second projection 156 extends toward the high-G wall 144 so as to form a constricted passage 158 (FIG. 10) through which the RBC layer 142 must flow to reach the red cell outlet port 66. FIG. 14 best illustrates the relationship between the second projection 156 and the high-G wall 144. The distance between the high-G wall 144 and the low-G wall 146 is indicated at "X" in FIG. 14. The distance between an outer surface of the second projection 156 and the high-G wall is indicated at "Y" in FIG. 14. In one embodiment, the ratio of Y to X is between approximately 0.01 and approximately 0.99. In another embodiment, the ratio of Y to X is between approximately 0.35 and approximately 0.75. In yet another embodiment, it has been found that a ratio of Y to X between approximately 0.45 and approximately 0.65 may be advantageous. For example, testing was performed on a centrifuge having a distance X between its high-G wall 144 and low-G wall 146 of approximately 0.233 inch and a distance Y between its second projection 156 and high-G wall 144 of approximately 0.133 inch, resulting in a Y to X ratio of approximately 0.57. Surprisingly, it was found that most of the platelets and white blood cells were transported out of the chamber for return to the patient mixed with the red blood cells without any loss of plasma separation efficiency. In carrying out a blood separation procedure using a centrifuge with such a configuration, the mean plasma removal efficiency was found to be approximately 80% in one study and approximately 81.9% in another study, while the mean platelet loss was found to be approximately $1.21 \times 10^{10}$ platelets per liter in one study and approximately $1.15 \times 10^{10}$ platelets per liter in another study, both of which values are improved compared to a centrifuge lacking a second projection 156.

The second projection 156 is present at or adjacent to the low-G wall 146 to intercept the plasma layer 148 flowing toward the red cell outlet port 66, as shown in FIG. 10. Rather than flowing through the constricted passage 158 to the red cell outlet port 66, the plasma layer 148 is intercepted by the second projection 156 and redirected to instead flow past the first projection 152 and into the plasma outlet port 68, thereby increasing the plasma collection efficiency of the centrifuge 52. As an additional benefit, if the centrifuge 52 is being used in a therapeutic plasma exchange procedure, the redirection of plasma from the path 86 to the plasma outlet port 68 will result in additional plasma being treated by an associated adsorption device, resulting in improved health benefits for the patient.

For improved transfer of plasma from the RBC path 86 to the plasma path 88, the second projection 156 may be oriented with one end positioned at or adjacent to the lower end of the interior seal 82 between the outlet ports 66 and 68. The other end of the second projection 156 may be positioned at or adjacent to the other interior seal 84 which defines the RBC path 86. If one end of the second projection 156 is located at or adjacent to the interior seal 84, plasma intercepted by the second projection 156 will be unable to move in that direction (due to the presence of the interior seal 84) and will instead be forced to flow toward the plasma path 88. One end of the first projection 152 may be substantially angularly aligned with the second projection 156 or be positioned at substantially the same location, as shown in FIGS. 11 and 13, to promote the transfer of red cells from the first projection 152 to the second projection 156 (and ultimately to the red cell outlet port 66) and the transfer of plasma from the second projection 156 to the first projection 152 (and ultimately to the plasma outlet port 68).

As for the platelets and white cells separated from the RBC and plasma layers 142 and 148, positioning the outlet ports 66 and 68 away from the inlet port 70 allows them to settle into the interface layer 150 by the time they reach the region leading to the paths 86 and 88. The first and second projections 152 and 156 are configured and oriented such that, during a therapeutic plasma exchange procedure or the like, the interface layer 150 will be prevented from entering the plasma outlet port 68 and will instead be redirected by the first projection 152 to flow beyond the second projection 156 and into the red cell outlet port 66.

Aspects of the present subject matter described above may be beneficial alone or in combination with one or more other aspects. Without limiting the foregoing description, in accordance with one aspect of the subject matter herein, there is provided a centrifugation system which includes the combination of a centrifuge and a separation chamber. The centrifuge is configured to separate blood components from blood by rotation about a rotational axis and comprises a generally annular low-G wall and a generally annular high-G wall which is located farther from the rotational axis than the low-G wall. The high-G wall includes a first projection extending toward the low-G wall and the low-G wall includes a second projection extending toward the high-G wall. The separation chamber includes multiple stages and is configured to be received in the centrifuge between the low-G and high-G walls. One of the stages of the separation chamber comprises an inlet port configured for flowing blood into the separation chamber, a plasma outlet port to transport a separated blood component substantially comprising plasma out of the separation chamber, and a red cell outlet port to transport a separated blood component substantially comprising red blood cells out of the separation chamber. When the separation chamber is received in the centrifuge between the low-G and high-G walls, the first projection is oriented so as to extend into the path of separated blood components flowing toward the plasma outlet port and prevent the separated blood component substantially comprising red blood cells from flowing into the plasma outlet port. The second projection is oriented so as to extend into the path of separated blood components flowing toward the red cell outlet port and prevent the separated blood component substantially comprising plasma from flowing into the red cell outlet port.

In accordance with another aspect which may be used or combined with the preceding aspect, the first projection is oriented at an angle with respect to the rotational axis and the second projection is oriented substantially perpendicular to the rotational axis.

In accordance with another aspect which may be used or combined with any of the preceding aspects, one end of the first projection is substantially angularly aligned with one end of the second projection.

In accordance with another aspect which may be used or combined with any of the preceding aspects, the second projection is configured and oriented so as to prevent the separated blood component substantially comprising plasma from flowing into the red cell outlet port and redirect the separated blood component substantially comprising plasma to flow into the plasma outlet port.

In accordance with another aspect which may be used or combined with any of the preceding aspects, the separation chamber includes an interior seal positioned between the red cell outlet port and the plasma outlet port, with one end of the second projection being positioned at or adjacent to an end of the interior seal.

In accordance with another aspect which may be used or combined with any of the preceding aspects, the separation chamber includes a plurality of interior seals positioned between the red cell outlet port and the inlet and plasma outlet ports, with the ends of the second projection being positioned at or adjacent to the interior seals.

In accordance with another aspect which may be used or combined with any of the preceding aspects, the ratio of the distance between the low-G and high-G walls to the distance between the second projection and the high-G wall is between approximately 0.01 and approximately 0.99.

In accordance with another aspect which may be used or combined with any of the preceding aspects, the ratio of the distance between the low-G and high-G walls to the distance between the second projection and the high-G wall is between approximately 0.35 and approximately 0.75.

In accordance with another aspect which may be used or combined with any of the preceding aspects, the ratio of the distance between the low-G and high-G walls to the distance between the second projection and the high-G wall is between approximately 0.45 and approximately 0.65.

In accordance with another aspect, there is provided a centrifuge for separating blood components from blood by rotation about a rotational axis. The centrifuge comprises a generally annular low-G wall and a generally annular high-G wall located farther from the rotational axis than the low-G wall. The high-G wall includes a first projection extending toward the low-G wall and the low-G wall includes a second projection extending toward the high-G wall. One end of the first projection is substantially angularly aligned with one end of the second projection.

In accordance with another aspect which may be used or combined with the preceding aspect, the first projection is oriented at an angle with respect to the rotational axis and the second projection is oriented substantially perpendicular to the rotational axis.

In accordance with another aspect which may be used or combined with any of the preceding two aspects, the ratio of the distance between the low-G and high-G walls to the distance between the second projection and the high-G wall is between approximately 0.01 and approximately 0.99.

In accordance with another aspect which may be used or combined with any of the preceding three aspects, the ratio of the distance between the low-G and high-G walls to the distance between the second projection and the high-G wall is between approximately 0.35 and approximately 0.75.

In accordance with another aspect which may be used or combined with any of the preceding four aspects, the ratio of the distance between the low-G and high-G walls to the distance between the second projection and the high-G wall is between approximately 0.45 and approximately 0.65.

In accordance with another aspect, there is provided a method for centrifugally separating blood components from blood. The method includes flowing blood into a first stage of a multiple-stage separation chamber, the first stage having a plasma outlet port and a red cell outlet port. The separation chamber is rotated so as to separate the blood into a separated blood component substantially comprising plasma and a blood component substantially comprising red blood cells. The separated blood components flow along a path toward the plasma outlet port, with the path including a first projection which is oriented to prevent the separated blood component substantially comprising red blood cells from flowing into the plasma outlet port. The separated blood components also flow along a path toward the red cell outlet port, with the path including a second projection which is oriented to prevent the separated blood component substantially comprising plasma from flowing into the red cell outlet port.

In accordance with another aspect which may be used or combined with the preceding aspect, flowing the separated blood components along a path toward the red cell outlet port includes redirecting the separated blood component substantially comprising plasma to flow into the plasma outlet port.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A method of centrifugally separating blood components from blood, comprising:
   flowing blood into a first stage of a multiple-stage separation chamber, the first stage having a plasma outlet port and a red cell outlet port;
   rotating the separation chamber about a rotational axis so as to separate the blood into a separated blood component substantially comprising plasma and a blood component substantially comprising red blood cells;
   flowing the separated blood components along a path toward the plasma outlet port, wherein the path toward the plasma outlet port includes a first projection which is oriented to impede the separated blood component substantially comprising red blood cells from flowing into the plasma outlet port; and
   flowing the separated blood components along a path toward the red cell outlet port, wherein
      the path toward the red cell outlet port includes a second projection which is oriented to impede the separated blood component substantially comprising plasma from flowing into the red cell outlet port, and
      one end of the first projection is substantially aligned with one end of the second projection along a radius passing through the rotational axis.

2. The method of claim 1, wherein said flowing the separated blood components along a path toward the red cell outlet port includes redirecting the separated blood component substantially comprising plasma to flow into the plasma outlet port.

3. The method of claim 1, wherein the first projection is oriented at an angle with respect to the rotational axis and the second projection is oriented substantially perpendicular to the rotational axis.

4. The method of claim 1, wherein
   the separation chamber is positioned between low-G and high-G walls of a centrifuge,
   the first projection extends from the high-G wall toward the low-G wall, and
   the second projection extends from the low-G wall toward the high-G wall.

5. The method of claim 4, wherein the ratio of the distance between the second projection and the high-G wall to the distance between the low-G and high-G walls is between approximately 0.01 and approximately 0.99.

6. The method of claim 4, wherein the ratio of the distance between the second projection and the high-G wall to the distance between the low-G and high-G walls is between approximately 0.35 and approximately 0.75.

7. The method of claim 4, wherein the ratio of the distance between the second projection and the high-G wall to the distance between the low-G and high-G walls is between approximately 0.45 and approximately 0.65.

8. A method of centrifugally separating blood components from blood, comprising:
   flowing blood into a first stage of a multiple-stage separation chamber, the first stage having a plasma outlet port and a red cell outlet port;
   rotating the separation chamber so as to separate the blood into a separated blood component substantially comprising plasma and a blood component substantially comprising red blood cells;
   flowing the separated blood components along a path toward the plasma outlet port, wherein the path toward the plasma outlet port includes a first projection which is oriented to impede the separated blood component substantially comprising red blood cells from flowing into the plasma outlet port; and
   flowing the separated blood components along a path toward the red cell outlet port, wherein the path toward the red cell outlet port includes a second projection which is oriented to impede the separated blood component substantially comprising plasma from flowing into the red cell outlet port, and one end of the first projection is positioned directly adjacent to one end of the second projection.

9. The method of claim 8, wherein said flowing the separated blood components along a path toward the red cell outlet port includes redirecting the separated blood component substantially comprising plasma to flow into the plasma outlet port.

10. The method of claim 8, wherein
said rotating the separation chamber includes rotating the separation chamber about a rotational axis, and
the first projection is oriented at an angle with respect to the rotational axis and the second projection is oriented substantially perpendicular to the rotational axis.

11. The method of claim 8, wherein
the separation chamber is positioned between low-G and high-G walls of a centrifuge,
the first projection extends from the high-G wall toward the low-G wall, and
the second projection extends from the low-G wall toward the high-G wall.

12. The method of claim 11, wherein the ratio of the distance between the second projection and the high-G wall to the distance between the low-G and high-G walls is between approximately 0.01 and approximately 0.99.

13. The method of claim 11, wherein the ratio of the distance between the second projection and the high-G wall to the distance between the low-G and high-G walls is between approximately 0.35 and approximately 0.75.

14. The method of claim 11, wherein the ratio of the distance between the second projection and the high-G wall to the distance between the low-G and high-G walls is between approximately 0.45 and approximately 0.65.

15. A method of centrifugally separating blood components from blood in a centrifuge including a generally annular low-G wall and a generally annular high-G wall located farther from a rotational axis of the centrifuge to define a channel therebetween, the method comprising:
flowing blood into a first stage of a multiple-stage separation chamber at least partially received in the channel, the first stage having a plasma outlet port and a red cell outlet port;
rotating the separation chamber about the rotational axis so as to separate the blood into a separated blood component substantially comprising plasma and a blood component substantially comprising red blood cells;
flowing the separated blood components along a path toward the plasma outlet port, wherein the path toward the plasma outlet port includes a first projection which is oriented to impede the separated blood component substantially comprising red blood cells from flowing into the plasma outlet port; and
flowing the separated blood components along a path toward the red cell outlet port, wherein
the path toward the red cell outlet port includes a second projection which is oriented to impede the separated blood component substantially comprising plasma from flowing into the red cell outlet port, and
one end of the first projection is positioned substantially directly across the channel from one end of the second projection.

16. The method of claim 15, wherein said flowing the separated blood components along a path toward the red cell outlet port includes redirecting the separated blood component substantially comprising plasma to flow into the plasma outlet port.

17. The method of claim 15, wherein the first projection is oriented at an angle with respect to the rotational axis and the second projection is oriented substantially perpendicular to the rotational axis.

18. The method of claim 15, wherein
the first projection extends from the high-G wall toward the low-G wall, and
the second projection extends from the low-G wall toward the high-G wall.

19. The method of claim 18, wherein the ratio of the distance between the second projection and the high-G wall to the distance between the low-G and high-G walls is between approximately 0.01 and approximately 0.99.

20. The method of claim 18, wherein the ratio of the distance between the second projection and the high-G wall to the distance between the low-G and high-G walls is between approximately 0.35 and approximately 0.75.

21. The method of claim 18, wherein the ratio of the distance between the second projection and the high-G wall to the distance between the low-G and high-G walls is between approximately 0.45 and approximately 0.65.

* * * * *